United States Patent [19]

Shirasu et al.

[11] Patent Number: 4,744,251

[45] Date of Patent: May 17, 1988

[54] APPARATUS FOR EXAMINING TUBULAR MEMBERS DISPOSED IN AXIALLY PARALLEL RELATIONSHIP

[75] Inventors: Isao Shirasu; Toshio Sanagawa, both of Kobe, Japan

[73] Assignee: Mitsubishi Jukogyo Kabushiki Kaisha, Tokyo, Japan

[21] Appl. No.: 913,305

[22] Filed: Sep. 30, 1986

[30] Foreign Application Priority Data

Oct. 9, 1985 [JP] Japan .................. 60-153675[U]

[51] Int. Cl.$^4$ ............................................ G01N 29/00
[52] U.S. Cl. .................................... 73/622; 376/340
[58] Field of Search .................. 73/622, 588, 582; 376/340

[56] References Cited

U.S. PATENT DOCUMENTS 4,434,660 3/1984 Michaels et al. .................... 73/622

Primary Examiner—Jerry W. Myracle
Attorney, Agent, or Firm—Wenderoth, Lind & Ponack

[57] ABSTRACT

An apparatus for examining a circumferential surface of each of a plurality of tubular members disposed in axially parallel relationship with each other has a rail adapted to extend between adjacent tubular members; a truck movable on and along the rail, a support frame having mounts at each end tiltably mounting the support frame on the truck for tilting around an axis extending along the rail, and a tilting mechanism connected to the support frame for tilting the support frame. A semi-circular shaped beam is mounted on the support frame for rotation around an axis through the center of the circle on which the semi-circular shaped beam lies and open laterally of the rail, and a sensing element is disposed at a predetermined position on the semi-circular shaped beam. The semi-circular shaped beam is tilted down by tilting the support frame when the truck is moved along the rail from one tubular member to the next, and is tilted up so as to partially surround the tubular member for carrying out the examination.

6 Claims, 3 Drawing Sheets

2

APPARATUS FOR EXAMINING TUBULAR MEMBERS DISPOSED IN AXIALLY PARALLEL RELATIONSHIP

BACKGROUND OF THE INVENTION

1. Field of the Invention

This invention relates to an apparatus for examining tubular members disposed in axially parallel relationship with each other.

2. Description of the Prior Art

Generally, there are several spots in a nuclear/thermal power plant and the chemical plant, each including a number of tubular members disposed in axially parallel relationship with each oher at narrow intervals. For example, as shown in FIG. 6, a number of adapters 02 for mounting respective control rod drive units are provided in the upper section of a cap 01 of a pressurized water reactor, to the respective upper portions of these mounting adaptors 02 being welded individual control rod drive units 03 (only one being illustrated), so that they are disposed in axially parallel relationship or stand close together. Reference numeral 04 designates a drive shaft shroud tube.

In connection with such a structure, it is natural to examine the welded portions of the mounting adapters 02 and control rod drive units 03, however, because these control rod drive units 03 are disposed at narrow intervals it is impossible to position an ultrasonic flaw detector and the like at a predetermined position. Hence, in the prior art, these welded portions were inspected, for example, through visual examination using a mirror, or by pressurizing the inside of each tube and checking external leakage.

However, because the spot being subjected to examination is narrow, either of the aforementioned procedures is carried out only with considerable difficulty and it is hard to say that a trustworthy and sufficient examination can be performed. Further, there is the inconvenience that the working hours are limited because the work is performed in a radioactive atmosphere.

SUMMARY OF THE INVENTION

It is an object of the present invention to provide an apparatus for examining tubular members disposed in axially parallel relationship with each other, which performs examination reliably in the manner of remote control detection, thereby obviating the need of access of workers and preventing occurrence of their exposure and the like.

The feature of the present invention achieving the foregoing object resides in an apparatus for examining tubular members disposed in axially parallel relationship with each other which comprises a rail extending between adjacent tubular members, a truck movable on and along the rail, a support frame mounted tiltably on the truck, a semi-ring-like beam rotatably mounted on the support frame and open laterally, and a sensing element disposed at a predetermined position on the semi-ring-like beam.

The present apparatus thus configured operates in such a manner that at the time of passing between the tubular members the support frame is tilted to avoid interference with the tubular members, and at the time of examination the support frame is raised to cause the semi-ring-like beam to position around one tubular member and the semi-ring-like beam is rotated to examine the circumferential surface of the tubular member by means of the sensing element.

DESCRIPTION OF THE PREFERRED EMBODIMENT

Figure 1:
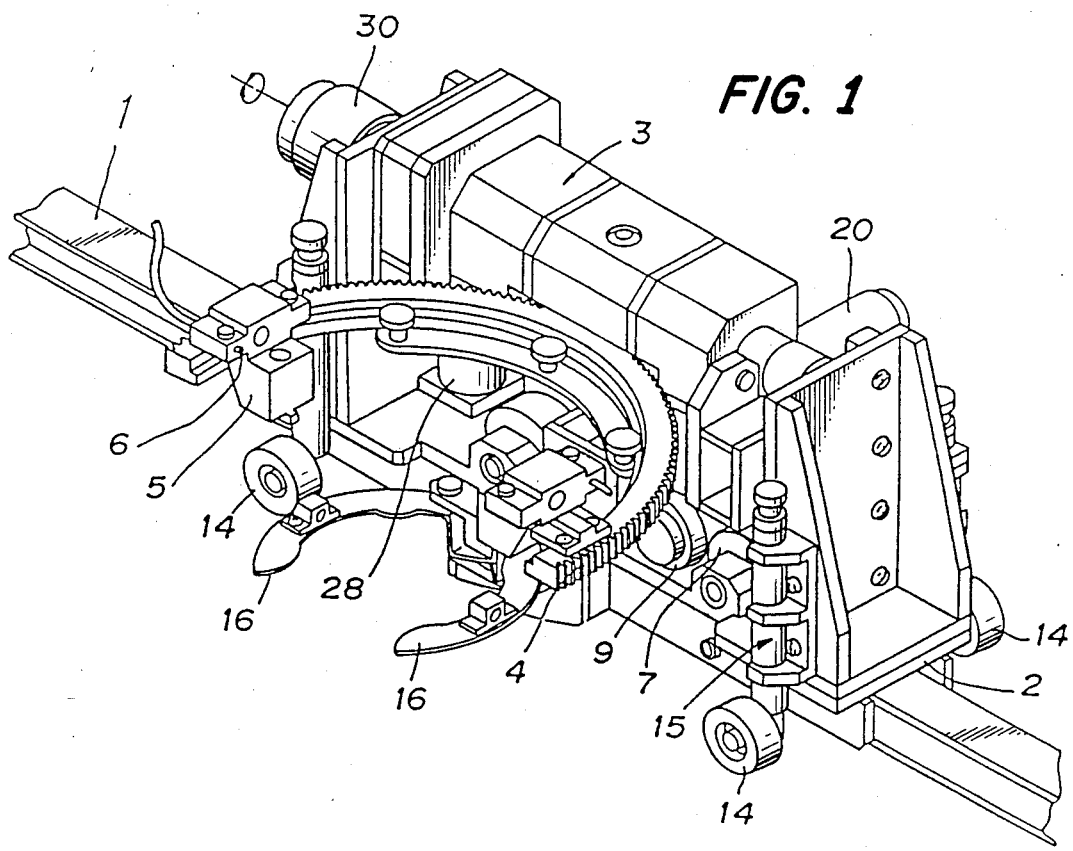
FIG. 1 is a perspective view of an embodiment of an apparatus according to the present invention for examining tubular members disposed in axially parallel relationship with each other.
Figure 2:
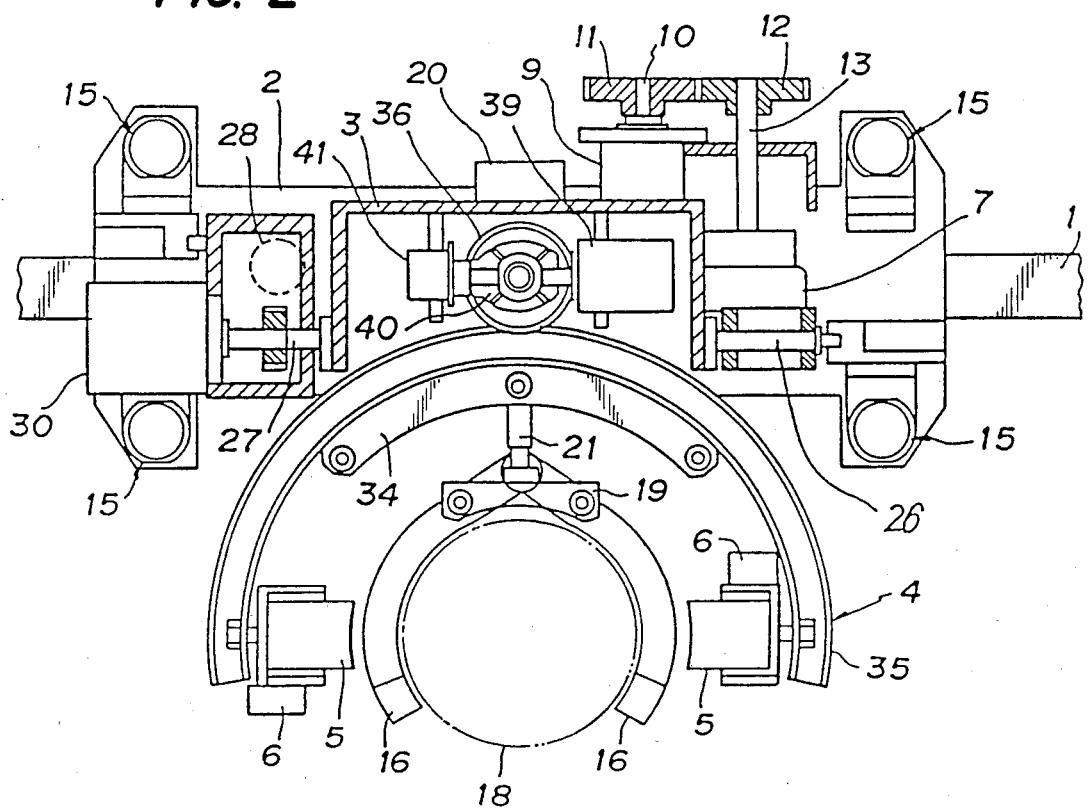
FIG. 2 is a plan view, partly in cross section, of the above.
Figure 3:
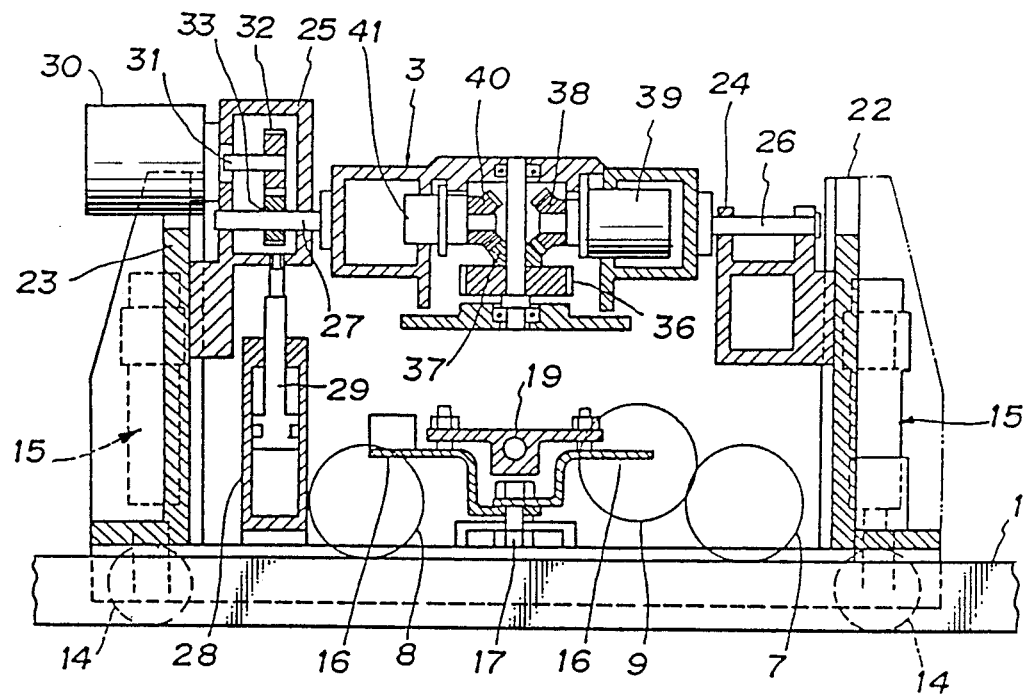
FIG. 3 is a sectional view of the above as viewed from the front.
Figure 4:
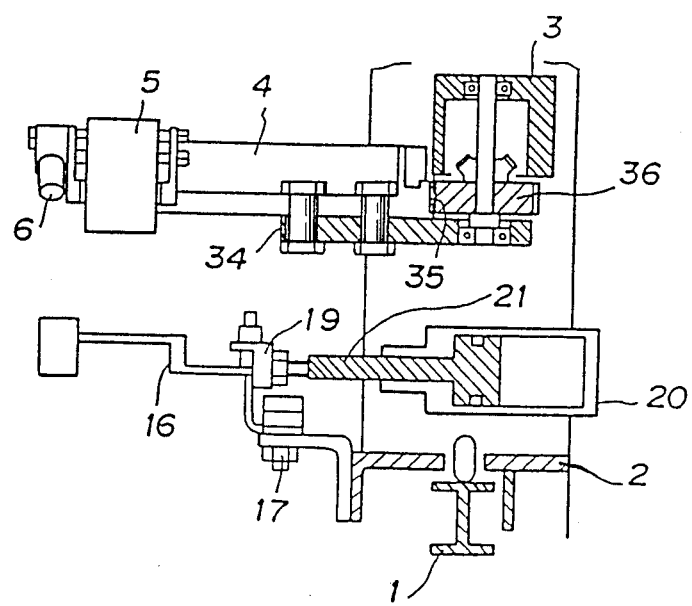
FIGS. 4 and 5 are sectional views of the above, as viewed from the side, showing different operating states.

An embodiment of the present invention will now be described with reference to FIGS. 1 through 5.

An apparatus according to the present invention comprises, as the important components, a rail 1 extending between and along tubes disposed in axially parallel relationship with each other at narrow intervals, a truck 2 movable on and along the rail 1, a gripping mechanism provided on the truck 2 for grasping an object tube to be examined to secure the truck 2 with respect to the object tube, a support frame 3 provided liftably and tiltably on the truck 2, a semi-ring-like beam 4 supported swivelably or rotatably by the support frame 3, and sensing elements, such as ultrasonic flaw detecting sensor 5 and fiberscope (or its objective) 6, provided at either end portion of the semi-ring-like beam 4.

The truck 2 is put on the rail 1 via a driving wheel 7 and a driven wheel (idler) 8 provided on the front and rear sides. A running motor 9 is equipped on the truck 2, its rotary shaft 10 being coupled with the driving wheel 7 via gears 11 and 12 and a rotary shaft 13. Hence, as the running motor 9 is energized the driving wheel 7 is driven and rotated so that the truck 2 moves on and along the rail 1. Resiliently and vertically movable guide rollers 14 are provided on either side of each of the front and rear sections of the truck 2. Reference numeral 15 designates a resiliency mechanism of the guide roller 14 (forming a guide leg).

A pair of circular grippers 16 is pivoted by a pin 17 on one side of the middle in the fore and aft direction of the truck 2. The grippers 16 are made arcuate as are able to grip the object tube 18 at its periphery. With these grippers 16 is coupled a piston rod 21 of a gripper opening/closing cylinder 20 via an opening/closing member 19. Thus, in response to actuation of the gripper opening/closing cylinder 20 the grippers 16 are opened/closed, whereby the object tube is gripped/released. As described above, the gripping mechanism is made up of the grippers 16, the gripper opening/closing cylinder 20, and the like.

The front and rear sections of the truck 2 have support mounts 22 and 23 provided vertically, a bearing mount 24 and a motor mount 25 are provided liftably along these support mounts 22 and 23, shafts 26 and 27 arranged in a straight line are rotatably provided on the bearing mount 24 and the motor mount 25, and the aforementioned support frame 3 serving also as a gear case is attached to the ends of these shafts 26 and 27.

With the motor mount 25 is coupled a piston rod 29 of a lifting cylindr 28 mounted on the truck 2, so that, as the piston rod 29 expands or contracts owing to actuation of the lifting cylinder 28, the motor mount 25, support frame 3, and bearing mount 24 are moved up or down in unison. Further, a tilting motor 30 is attached to the motor mount 25, and its rotary shaft 31 is coupled via gears 32 and 33 with the aforementioned shaft 27. Thus, in response to actuation of the tilting motor 30, the support frame 3 together with the shaft 27 is tilted about the shafts 26 and 27 via the gears 32 and 33. In short, a lifting mechanism of the support frame 3 is made up of the lifting cylinder 28, the motor mount 25, and the like, whereas a tilting mechanism of the support frame 3 is made up of the tilting motor 30, the gears 32 and 33, the shafts 26 and 27, and the like.

On the front side of the support frame 3 is provided a circular beam guide 34, on this beam guide 34 being supported the semi-ring-like beam 4. The beam 4 has teeth 35 formed on its outer periphery, a spur gear 36 in gear with the teeth 35 is supported inside the support frame 3, and a swiveling or rotating motor 39 is provided inside the support frame 3 which is equipped on its rotary shaft with a gear 38 being in gear with a bevel gear 37 integral with the spur gear 36. Thus, in response to actuation of the swiveling motor 39 and through gearing between the spur gear 36 and the teeth 35, the semi-ring-like beam 4 is driven and swiveled or rotated while being guided by the beam guide 34. As described above, to either end portion of the beam 4 are attached the ultrasonic flaw detecting sensor 5 and the fiberscope 6 functioning as the sensing element. Because the beam 4 performs examination about the whole circumferential surface of the object tube 18 while rotating in either circumferential direction, a semi-circular shape is enough therefor, but, the beam is elongated in practice by a length corresponding to a space for attaching the sensing element and the like. Incidentally, a position detector 41 is coupled via a bevel gear 40 with the spur gear 36, by which the location of the ultrasonic flaw detecting sensor 5 and fiberscope 6 provided on the beam 4 is detected.

The operation modes of the foregoing present apparatus will now be described.

Figure 5:
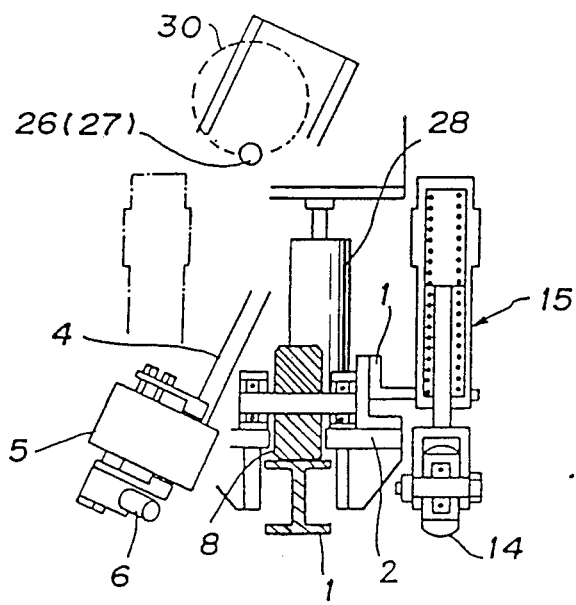
Figure 6:
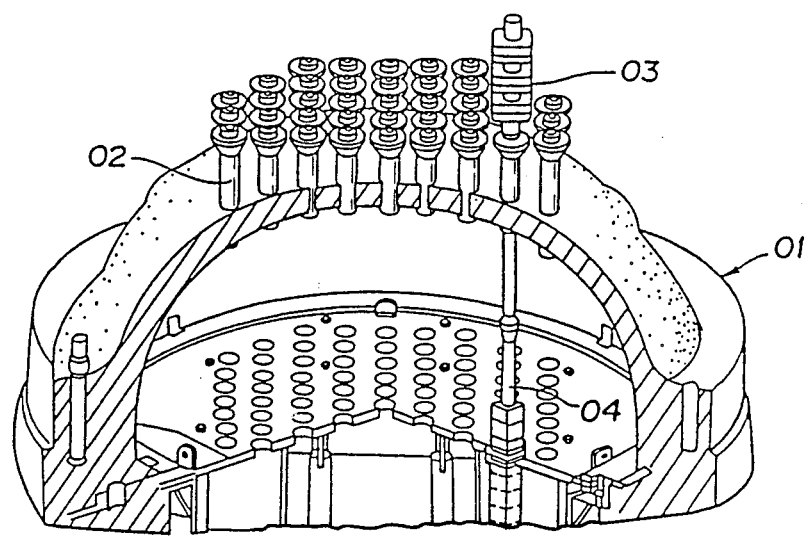
FIG. 6 is a perspective view, with portions broken away, of a cap section of a pressurized water reactor.

At the time of examining the welded portions of the tubes disposed in axially parallel relationship with each other at narrow intervals, in order to cause the truck 2 to move between the tubes, the beam 4 together with the support frame 3 is tilted by the tilting mechanism to make narrow the overall width of the apparatus as shown in FIG. 5 so that the apparatus will not interfere with the tubes, but pass between the tubes.

As the truck 2 comes near and stands beside the object tube 18, the beam 4 together with the support frame 3 is raised up so as to assume a horizontal position by the tilting mechanism. Then, the object tube 18 is gripped by the grippers 16 of the gripping mechanism, so that the truck 2 is secured with respect to the object tube 18. Thereafter, the lifting cylinder 28 of the lifting mechanism is actuated to set the beam 4 to a given height (at which the sensing element confronts the welded portion). In the thus attained state, the swiveling motor 39 is actuated to cause the beam 4 to rotate around the welded portion, whereby examination of the welded portion can be performed by means of the ultrasonic flaw detecting sensor 5 and fiberscope 6. Through forward and reverse rotation of the swiveling motor 39 the whole circumferential surface of the welded portion is examined by means of the ultrasonic flaw detecting sensor 5 and fiberscope 6.

After completion of examination, the grippers 16 are released to make free the truck 2, the beam 4 together with the support frrame 3 is moved down by the tilting mechanism, and the truck is caused tomove toward the object tube to be examined next while avoiding interference with the tubes.

Although the foregoing embodiment is equipped with the lifting mechanism for the support frame 3, this lifting mechanism may be omitted if desired. Further, the mechanism for tilting the support frame 3 and the mechanism for swiveling or rotating the beam 4 should not be limited to those of the foregoing embodiment and can take any modified configuration.

According to the apparatus of the present invention for examining tubular members disposed in axially parallel relationship, the semi-ring-like beam having the sensing element is tiltable, so that it can pass between the closely-standing tubular members with the beam down and perform examination with the beam raised up horizontally, whereby reliable examination can be achieved easily. Further, because examination is performed in the manner of remote control, the examination work can be performed even at a spot which is dangerous for workers to access.

What is claimed is:

1. An apparatus for examining a circumferential surface of each of a plurality of tubular members disposed in axially parallel relationship with each other, comprisin:
   a rail adapted to extend between adjacent tubular members;
   a truck movable on and along said rail;
   a support frame having mounts at each end tiltably mounted said support frame on said truck for tilting around an axis extending along said rail;
   a tilting mechanism connected to said support frame for tilting said support frame;
   a semi-circular shaped beam mounted on said support frame for rotation around an axis through the center of the circle on which said semi-circular shaped beam lies and open laterally of said rail; and
   a sensing element disposed at a predetermined position on said semi-circular shaped beam.

2. The apparatus as claimed in claim 1, characterized in that the sensing element is an ultrasonic probe.

3. The apparatus as claimed in claim 1, characterized in that the sensing element is an object of a fiberscope.

4. The apparatus as claimed in claim 3, further including an ultrasonic probe disposed on the semi-circular shaped beam.

5. The apparatus as claimed in claim 1, further including means for gripping one of the tubular members during the examination thereof.

6. The apparatus as claimed in claim 5, wherein the truck is provided with guide legs on both sides thereof.

* * * * *